United States Patent [19]
Fullemann

[11] Patent Number: 5,707,589
[45] Date of Patent: Jan. 13, 1998

[54] FUNNEL-SHAPED SAMPLE-VIAL SEPTUM WITH MEMBRANE COVERED DIFFUSION-BARRIER SECTION

[75] Inventor: James Steven Fullemann, deceased, late of Half Moon Bay, Calif., by Ivan Crockett, legal representative

[73] Assignee: Merlin Instrument Company, Half Moon Bay, Calif.

[21] Appl. No.: 630,692

[22] Filed: Apr. 12, 1996

[51] Int. Cl.$^6$ .................................................. B01D 15/08
[52] U.S. Cl. ........................... 422/99; 422/100; 422/101; 422/103; 422/104; 215/247; 215/310; 55/386; 210/198.2
[58] Field of Search .................... 422/99–104; 436/177, 436/178, 180; 215/247, 310; 55/386; 210/198.2

[56] References Cited

U.S. PATENT DOCUMENTS

| | | | |
|---|---|---|---|
| 3,814,248 | 6/1974 | Lawhead | 210/83 |
| 4,573,994 | 3/1986 | Fischell et al. | 604/891 |
| 4,889,256 | 12/1989 | Fowles | 220/306 |
| 4,935,010 | 6/1990 | Cox et al. | 604/122 |
| 4,954,149 | 9/1990 | Fullemann | 55/386 |
| 5,358,613 | 10/1994 | Schneider et al. | 204/180.1 |
| 5,397,303 | 3/1995 | Sancoff et al. | 604/82 |
| 5,553,748 | 9/1996 | Battle | 222/94 |
| 5,569,225 | 10/1996 | Fleury | 604/323 |
| 5,578,459 | 11/1996 | Gordon et al. | 135/29 |

OTHER PUBLICATIONS

Alltech Catalog, date unknown, selected pages, 328, 329, 331, 334–341.
Hewlett–Packard Catalog, date unknown, selected pages, 18–23, 26.
Supelco Catalog, date unknown, selected pages, 623, 624, 626–628.

*Primary Examiner*—Harold Y. Pyon
*Attorney, Agent, or Firm*—Clifton L. Anderson

[57] ABSTRACT

A funnel-shaped monolithic low-density polyethylene sample-vial septum comprises a flange, a capture wall, a diffusion-barrier wall, and a membrane. The capture wall is conical, extending from its truncated apex at the diffusion barrier wall to its mouth about which the flange is disposed. The membrane is disposed at the end of the diffusion-barrier wall away from the capture wall. This structure defines a septum aperture, including a conical capture section, defined by the capture wall, and a cylindrical diffusion-barrier section, defined by the diffusion-barrier wall. The 7.0 mm length of the diffusion-barrier section is 12/mm times the square of its diameter 0.76 mm. The diameter of the diffusion-barrier section which is selected to be 0.05 mm greater than the diameter of the largest needle to be used with the septum, i.e., a 22 gauge needle typically used for liquid chromatography. The minimum thickness of the membrane is 0.05 mm so that a blunt 26 gauge needle will not be damaged while piercing the membrane. The membrane has a curved surface facing the capture section. The radius of curvature of this surface is 7.0 mm, set equal to the barrier section length. This is a result of a molding tool tip that is curved so that if misaligned, the desired minimum membrane thickness is still achieved. Prior to piercing, the membrane serves as a solid barrier to evaporative sample loss. After piercing, the long diffusion-barrier section serves as an effective barrier to evaporative sample loss.

7 Claims, 4 Drawing Sheets

FUNNEL-SHAPED SAMPLE-VIAL SEPTUM WITH MEMBRANE COVERED DIFFUSION-BARRIER SECTION

BACKGROUND OF THE INVENTION

The present invention relates to chemical analytical systems and, more particularly, to a septum for a sample vial. A major objective of the present invention is to provide an improved and economical sample vial septum.

Many recent advances in the medical, life and environmental sciences have relied on precise chemical analysis of liquid samples comprising many constituent components. Typically, samples are placed in small glass or plastic vials having capacities ranging form several microliters to several milliliters. To provide high throughput, analytical chemical techniques can be automated. As many as hundreds of samples can be prepared and loaded for automated analysis, which can take as much as a day to complete. Thus, samples are held in vials for hours or days before analysis actually takes place.

Typically, the sample in a vial is sealed at its top by a septum, which is in turn held in place by a vial cap. The purpose of the septum is to protect the sample in the vial from evaporative loss, spillage, and contamination, while providing convenient access with a syringe. The syringe can be used to remove a precise amount of the sample from the vial. Typically, the syringe needle pierces the septum, the desired aliquot of sample is withdrawn, and the needle is withdrawn from the septum. The aliquot of sample in the syringe can then be injected into an analytical system, such as a gas chromatograph, which may have its own septum.

Most septa are rubber, e.g., silicon rubber, butyl rubber, fluorocarbon rubber (such as Dupont Viton®) membranes; they are typically held in place by crimped, screw-on, or snap-on vial caps. Rubber is elastomeric so that it can reseal after a piercing needle is withdrawn, thus preserving the sample in the vial for subsequent use. A related disadvantage is that the rubber effectively forms an airtight seal around the syringe needle as the sample is withdrawn from the vial. As a result, a partial vacuum can form in the vial as the sample is withdrawn. This vacuum can make it more difficult to fill a syringe reliably when subsequent samples are withdrawn.

There are other disadvantages to rubber septa. The rubber can interact with sample components deleteriously. Rubber, because of its nature and formulation, has a variety of lower molecular weight compounds trapped in its matrix. If the sample solution contacts the rubber, these compounds can contaminate the sample and interfere with the analysis. Septum-sample contact can occur through tipping of the vial, splashing of the sample liquid, and abrasion of the septum as a needle slides through it. Such contamination is becoming an increasingly significant problem as advances in analytical instrumentation provide increased sensitivity. In addition, some volatile solvents and sample components can dissolve into the rubber, diffuse through the rubber, and evaporate to the environment; this can contribute to loss of sample and contamination of the local environment.

Polymeric septa, e.g., of pure polyethylene, polypropylene, or polytetrafluoroethylene (PFTE), address many of the problems afflicting rubber septum. Contamination is greatly reduced. Diffusion through an unpierced polymeric septum is negligible. Since a polymeric septum does not seal tightly against a syringe needle, no partial vacuum forms to interfere with subsequent sample extractions. On the other hand, since a polymeric septum does not effectively reseal after the needle is withdrawn, evaporative sample loss can be a problem.

Polymer-faced rubber septa combine some of the advantages of polymeric septa with those of rubber septum. The rubber effectively reseals the vial, which preserves the sample, but raises the problem of partial vacuum formation. The polymer is disposed between the rubber and the sample so that diffusion and contamination are limited. However, once the septum is pierced, rubber is exposed. The problems or sample loss and contamination are reintroduced once the septum is pierced. While these problems are reduced relative to a pure rubber septum, they can still be unacceptable.

In addition to the foregoing concerns, septa must be designed to avoid needle bending and breakage. Commonly used in gas chromatography, 50 mm long, 26-gauge needles can bend under the force required to penetrate a septum. The problem is reduced for sharp needles, but blunt needles are preferred for their more favorable spray patterns upon injection of the sample into an analytical instrument, especially a gas chromatograph. The problem with needle bending is addressed primarily by using thin membranes. Rubber septa are typically between 1 and 2 millimeters thick. Polymer septa are typically about 0.25 millimeters thick. Rubber and polymer-face rubber septa can be pre-slit, but there is a problem aligning the needle with the slit.

A final consideration is price. Sample vial septa are used for one sample and then discarded. Rubber and polymer membranes can be made sufficiently inexpensive. However, more sophisticated seals, such as the two-part gas chromatography injection septum described in U.S. Pat. No. 4,954,149 to Fullemann would not be cost effective as sample vial seals. What is needed is an economical septum which provides for reduced sample contamination and loss, while avoiding vacuum buildup in the sample vial. In addition, the septum should be designed to avoid damage to syringe needles.

SUMMARY OF THE INVENTION

The present invention provides a funnel-shaped septum comprising a flange, a capture wall, a diffusion barrier wall, and a membrane. The septum defines a septum aperture; the diffusion barrier wall defines a capture section of the septum aperture, and the diffusion-barrier wall defines a diffusion-barrier section of the septum aperture. The capture wall extends between the flange and the diffusion barrier wall. The hydraulic diameter of the capture section at the flange is at least twice the hydraulic diameter of the capture section adjacent to the barrier section. The length in millimeters of the diffusion-barrier section is at least six times, and is preferably about twelve times, its average hydraulic diameter in millimeters.

The membrane is disposed in the diffusion barrier aperture so as to provide a solid barrier to sample loss. Sample is extracted from the vial by inserting a syringe needle through the membrane and withdrawing sample into the syringe. In the process, the membrane is pierced; from this time on, the diffusion barrier section effectively limits diffusion of sample from the vial.

The septum is preferably monolithic and preferably formed of polymer. By "monolithic" is meant that it is fabricated from a single piece of material, as by molding or machining, rather than formed by assembling or fusing separate components. The monolithic structure includes not only the walls of the aperture, but the flange and the membrane as well.

The preferred material is linear low-density polyethylene in the 0.91 to 0.93 g/cm$^3$ range. Polyethylene can be obtained relatively free of low-molecular weight compounds that could contaminate the sample. In addition, polyethylene tears in a ductile manner. It does not shatter or crack in a brittle manner, so pieces are unlikely to wind up in the sample or be carried by the needle to the analytic instrument.

The flange, which extends radially outward from the longitudinal axis of the aperture, seals against the top of a sample vial. Ribs can be formed on the flange to aid the sealing. The flange is deformed by a screw-on or crimp-on cap so as to force it into intimate contact with the top surface of a glass or plastic vial.

The walls of the capture section are tapered to guide a misaligned syringe needle into the diffusion barrier section. The taper can be conical or be a more complex shape. The slope of the barrier section is selected so that a needle slides without sticking on the capture wall.

The funnel-shaped polymer septum shares the pre-pierced low-contamination and low-sample-loss advantages of the polymer-membrane and polymer-faced-rubber-membrane prior art septa. Since the funnel-shaped septum does not form an airtight seal against a syringe needle, it shares with the polymer-membrane septum the advantage that a partial vacuum does not form in the vial and interfere with subsequent sample extractions.

The polymer membrane of the funnel-shaped septum does not reseal after a needle is withdrawn. The inference could be drawn that sample would evaporate through the pierced funnel-shaped septum at a rate comparable to that of the pierced polymer membrane septum. Surprisingly, the diffusion rate through a pierced polymer funnel-shaped septum is more comparable to the diffusion rate through a pierced polymer-faced rubber membrane septum. This surprising result is attributed to the relatively long diffusion path through the barrier section of the funnel-shaped septum. Thus, the present invention provides the advantages of the polymer-faced rubber membrane septum, but with reduced exposure to sample contamination.

Serendipitously, the funnel-shaped septum offers an additional advantage in handling small quantity samples. Microliter-sized samples would only coat the bottom of a standard sample vial, making it difficult for a syringe to extract it. To facilitate extraction of small volume samples, small-volume inserts are inserted into standard sample vials so that the sample level is high enough for convenient extraction. Because the increased sample level is achieved at the expense of sample cross-sectional area, alignment of the syringe needle and the small volume insert is critical. The capture section of the funnel-shaped septum is designed to center the needle on the sample vial. However, if the small volume insert is not centered in the vial, the needle is not aligned with the sample. Since it protrudes into the interior of the sample vial, the funnel-shaped septum can be used to center the insert within the vial, thus optimizing the geometry for needle alignment and sample extraction.

Thus, the present invention provides a septum which is relatively free of both sample contamination and sample loss through diffusion. In addition, the relatively small membrane can be made thin enough to minimize needle bending. In addition, the novel septum can be molded as a single piece, making it economical to manufacture. These and other features and advantages are apparent from the description below with reference to the following drawings.

DESCRIPTION OF THE PREFERRED EMBODIMENTS

Figure 1:
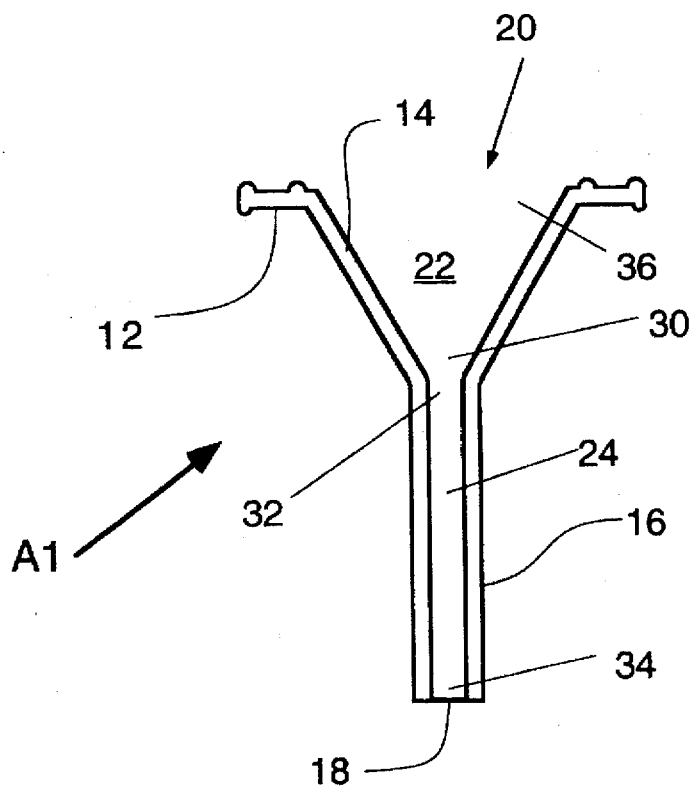
FIG. 1 is a slice-sectional view of a sample-vial septum in accordance with the present invention.
Figure 2:
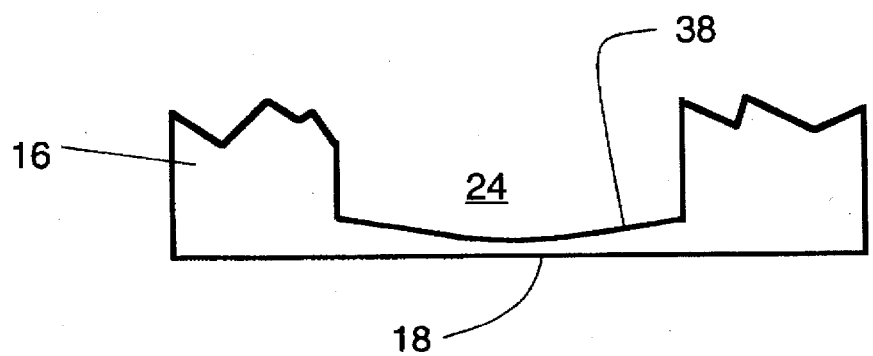
FIG. 2 is a slice-sectional view of a tip of the sample-vial septum of FIG. 1.

In accordance with the present invention, a monolithic funnel-shaped sample-vial septum A1 comprises a flange 12, a capture wall 14, a diffusion barrier wall 16, and a membrane 18, as shown in FIG. 1. Collectively, these elements define a septum aperture 20 comprising a capture section 22, defined by capture wall 14, and a diffusion-barrier section 24, defined by diffusion barrier wall 16. Capture wall 14 is generally conical with its apex end 30 truncated where it merges with one end 32 of cylindrical diffusion barrier wall 16. The other end 34 of the diffusion barrier wall 16 is sealed by membrane 18, as shown in FIG. 2. The wide end 36 of capture wall 14 is ringed by annular flange 12.

Septum A1 is molded as a single piece using linear low-density polyethylene (e.g., Dowlex LLDPE #2505 available from Dow Chemical); the low-density polyethylene is produced by a high-pressure polymerization that yields a relatively soft material. Polyethylene, as well as alternative polymers, provide an effective and contamination-free solid diffusion barrier for long-term sample storage. Low-density polyethylene is preferred because membrane 18 is more easily pierced by a syringe needle. Accordingly, membranes can be made thicker, e.g., with a range of 0.025 to 0.15 millimeters (mm), with 0.05 mm preferred, and still be pierced by a blunt tip 26 gauge needle. The thicker membrane eases constraints on the molding process, providing higher yields and a lower manufacturing costs. In an alternative embodiment, the membrane is molded with a thin perimeter to assist its tearing away like a flap during needle insertion. Membrane 18 is at the bottom end 34 of barrier section 24 for ease in molding; alternatively, the membrane can be at other locations within a barrier section.

The injection mold used to form septum A1 includes a pin that defines barrier section 24. This pin has a tip with a radius of curvature roughly equal to the length of diffusion barrier section 24, in this case 7.0 mm. Thus, the desired minimum membrane thickness is achieved even when the tool used to mold the interior of a septum A1 is somewhat misaligned. The curvature of the molding tool is imposed on the top surface 38 of membrane 18.

Figure 3:
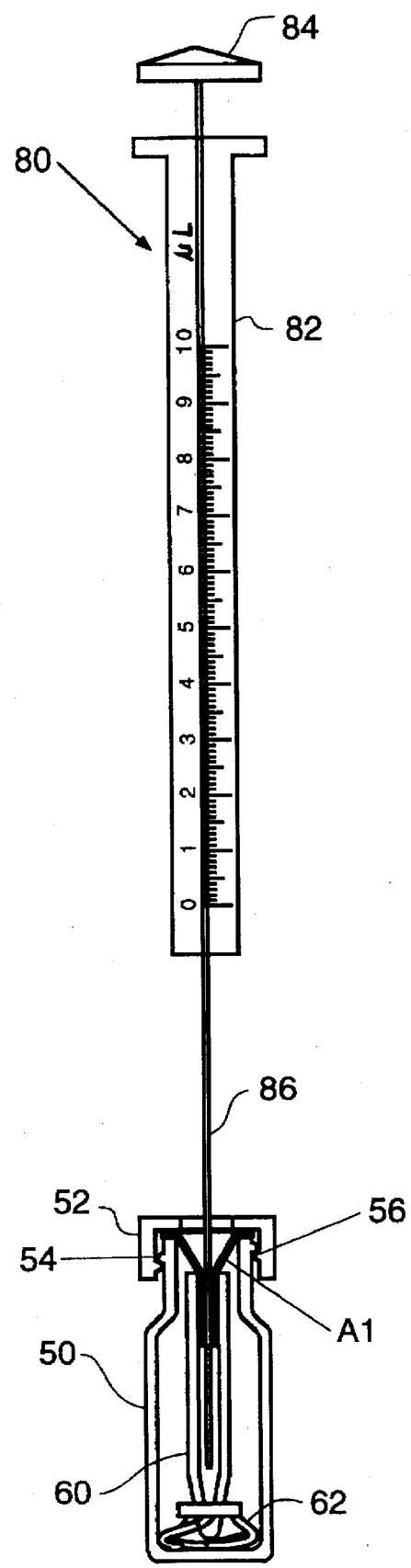
FIG. 3 is a slice-sectional view of a screw-cap sample-vial assembly including the septum of FIG. 1 and showing a syringe with a needle inserted through the septum.
Figure 4:
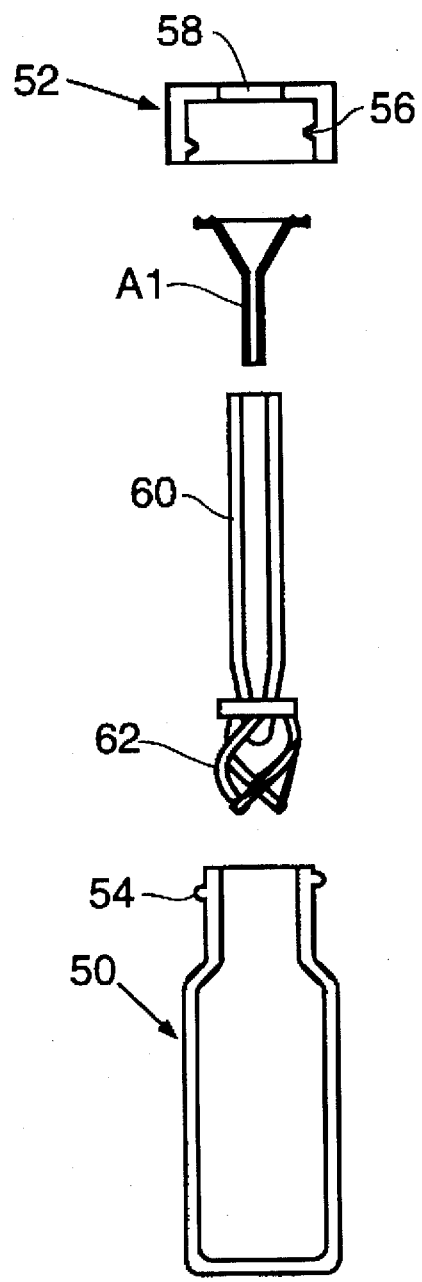
FIG. 4 is an exploded view of the sample-vial assembly of FIG. 3.
Figure 5:
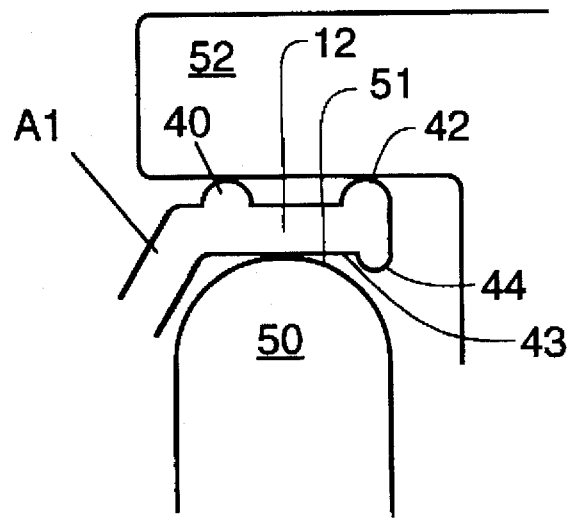
FIG. 5 is a detail of FIG. 3 showing the engagement of the septum by a sample vial and a cap of the sample-vial assembly of FIG. 3.
Figure 6:
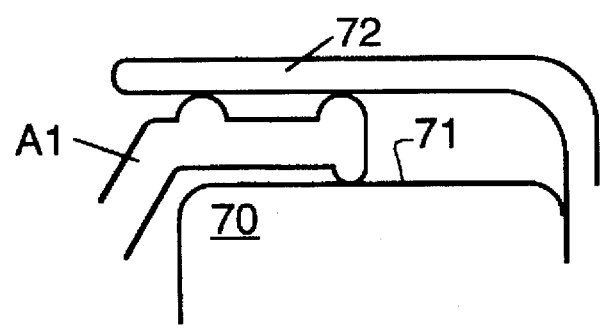
FIG. 6 is a detail of a crimp-cap sample-vial assembly showing the engagement of the septum of FIG. 1 by a crimp-cap sample vial and a crimped-on cap.

Septum A1 is used to seal and provide access to a sample vial 50, as shown in FIG. 3. Septum A1 is held in place by a sample-vial cap 52. Sample vial 50 and cap 52 have mating threads 54 and 56 so that septum A1 is fixed in place as cap 52 is screwed onto sample vial 50. In the present case, a 100-µL small-volume insert 60 is used to make a low-volume sample more accessible. As best seen in FIG. 4, small volume insert 60 has plastic legs 62 that are compressed by septum A1 as cap 52 is screwed onto sample vial 50. In addition, cap 52 compresses an inner upper rib 40 and an outer upper rib 42 of septum flange 12 to force a lower surface 43 of septum flange 12 against the top rim 51 of sample vial 50 to provide an airtight seal between septum A1 and vial 50, as shown in FIG. 5. Ribs 40 and 42 can be deformed by varying amounts around their circumferences to compensate for unevenness in top rim 51. Septum A1 is shown in the context of a crimp-cap vial 70 and cap 72 in FIG. 6. Upper outer rib 42 of setpum flange 12 forces lower rib 44 against top surface 71 of crimp-on vial 70.

A 10 μL syringe 80, shown in FIG. 3, is used to withdraw the contents of sample vial 50 and insert 60. Syringe 80 includes a graduated body 82, a plunger 84, and a blunt 26-gauge needle 86. Needle 86 is inserted through a 5.5 mm diameter aperture 58 in cap 52. If needle 86 is misaligned, it is guided by the conical capture wall 14 into barrier section 24. If this is the first time sample is removed through septum A1, needle 86 pierces membrane 18. Prior to this piercing, membrane 18 completes a solid seal between the interior and exterior of vial 50. After needle 86 is removed, the barrier is no longer solid. However, the dimensions of barrier section 24 are selected so that sample loss through diffusion is at an acceptable level.

Preferably, the length in millimeters of barrier section 24 is twelve times the square of its inner diameter in millimeters. Expressed otherwise, the length of the barrier section is 12/mm times the square of its inner diameter. (Note that the magnitude of the factor is different for different units of length.) This factor can be varied, e.g., from 9/mm to 15/mm, according to the volatility of a sample and the quantity of sample loss considered acceptable. To save costs, the minimum factor can be as low as about 6/mm.

The inner diameter of barrier wall 16 should allow some clearance for the largest needle to be inserted through septum A1. This can be accomplished by setting the inner diameter of barrier wall 16 to be about 0.050 mm greater than the maximum needle diameter. Septum A1 is designed to accommodate the 22 gauge needles used for liquid chromatography as well as the smaller 23 and 26 gauge needles used for gas chromatography. The diameter of a 22 gauge needle is 0.71 mm so that the inner diameter of barrier section is 0.76 mm, and the barrier section length is 7.0 mm. The surface tension of the sample should prevent its flow through the diffusion barrier section in the event of misorientation of sample vial 50.

The wall thickness for setpum A1 is 0.36 mm, selected from a preferred range of 0.25 to 0.50. The preferred thickness is largely determined by molding considerations. Thinner is better to cool the parts in the mode quicker to improve mode cycle times. However, if the wall is too thin, the part may be too flimsy to eject from the mold without tearing.

The minimum diameter of the capture section 22 matches the diameter of the diffusion-barrier section 24. The maximum diameter of capture section 22 is selected to be large enough to capture a syringe needle that suffers from a maximum expected misalignment. In practice, needle misalignment is no greater than that permitted by cap aperture 58. Accordingly, the maximum diameter of capture section 22 is selected to match the cap aperture diameter, which is 5.5 mm. More generally, the range of the maximum diameter of a capture section can vary between 4.5 mm to 6.5 mm, for example, to achieve a greater or lesser total septum length.

For septum A1, capture wall 14 increases in diameter linearly from its minimum diameter to its maximum diameter. The interior angle of the capture section is 60° so that syringe needle 86 can slide into the barrier section without sticking or jamming. These specifications yield a capture section length of 4.0 mm. Other suitable angles in the range of 50° to 65° can be selected, for example, to provide shorter or longer capture sections, e.g., 3.0 to 6.0 mm, and thus lesser or greater total septum lengths. The septum length can be varied, for example, to provide more effective alignment of a small-volume insert. In an alternative embodiment, the interior angle is varied within this angular range along the capture section.

Septum flange 12 has a diameter of 8.9 mm, selected from a range of 6.9 mm to 9.4 mm so that it sits on top of vial 50 and within cap 52. Upper ribs 40 and 42 have a radii of 0.2 mm selected from a range of 0.1 to 0.4 mm. Outer upper rib 42 has a major diameter of 8.5 mm, selected to be 0 to 2 mm less than the outside diameter of flange 12. Inner upper rib 40 has a major diameter of 6.35 selected to be between 0 and 2 mm greater than the maximum capture diameter. Lower rib 44 is aligned with upper outer sealing rib 42, but could be located elsewhere as long as it does not interfere with a rib on the top of the vial. Alternative embodiments employ a second lower rib radially inward of an outer lower rib.

Other embodiments of the invention utilize other polymer materials. Other suitable linear low-density polyethylenes are available with densities of 0.917–0.930 grams per cubic centimeter (g/cc), yield strengths between 1.7 and 2.5 kilopounds per squre inch (kpsi), and ultimate tensile strengths of 1.1–3.4 kpsi. Other low-density polyethylenes with sufficient solvent resistance can be used. In addition, there are suitable ultra-low density polyethylenes ULDPE (e.g., Attane, available from Dow Chemical) with densities of 0.912, yield strengths of 1.1–1.3 kpsi, and ultimate tensile strengths of 2.5–3.9 kpsi. In addition, a high density polyethylene with sufficient low yield strength can be used. Polymers other than polyethylene with the appropriate yield strength and solvent resistance can be used.

Different funnel-shaped septa can have different dimensions. While the preferred embodiment has cylindrical symmetry, other embodiments use other geometries. In these cases, the dimensions for radii and diameters are hydraulic diameters and radii. These and other variations upon and modifications to the preferred embodiment are provided for by the present invention, the scope of which is limited only by the following claims.

We claim:

1. A septum comprising:
   a diffusion barrier wall defining a diffusion barrier aperture having a maximum hydraulic diameter and a length in mm that is at least 6/mm times the square of said maximum hydraulic diameter in mm;
   a vapor impermeable seal across said diffusion barrier aperture;
   a capture wall having a first capture wall end and a second capture wall end, said first capture wall end being adjacent to said diffusion barrier section and having a first capture hydraulic diameter, said second capture wall end having a second capture hydraulic diameter more than twice said first capture hydraulic diameter; and
   a flange adjacent said second capture wall end and extending radially outward therefrom.

2. A septum as recited in claim 1 wherein said diffusion barrier wall, said seal, said capture wall, and said flange are molded together of polymeric material.

3. A septum as recited in claim 2 wherein said polymeric material is polyethylene.

4. A septum as recited in claim 3 wherein said polyethylene is low-density polyethylene.

5. A septum as recited in claim 4 wherein said seal has a thickness between 0.025 mm and 0.15 mm.

6. A septum as recited in claim 2 wherein said seal has a curved surface facing said capture wall.

7. A septum as recited in claim 6 wherein said curved surface has a radius of curvature between 10/mm and 15/mm times the square of said maximum hydraulic diameter.

* * * * *